United States Patent [19]  [11]  4,128,661
Schulthess et al.  [45]  Dec. 5, 1978

[54] (BIS-DIETHYLAMINE)2,5-DIHYDROXY-BENZENE-1,4-DISULFONATE, USEFUL AS A MEDICAMENT AGAINST GLAUCOMA

[75] Inventors: Adrian Schulthess, Vaud; Alfred de Courten, Geneve, all of Switzerland

[73] Assignee: Laboratories OM Societe Anonyme, Geneve, Switzerland

[21] Appl. No.: 853,912

[22] Filed: Nov. 22, 1977

[51] Int. Cl.$^2$ .......................................... A61K 31/205
[52] U.S. Cl. ................................................... 424/316
[58] Field of Search ......................................... 424/316

[56] References Cited

U.S. PATENT DOCUMENTS

| 3,351,526 | 11/1967 | Subirana | 424/316 |
| 3,436,462 | 4/1969 | Subirana | 424/316 |
| 3,873,606 | 3/1975 | Subirana | 424/316 |
| 4,005,220 | 1/1977 | Subirana | 424/316 |
| 4,038,390 | 7/1977 | Subirana | 424/316 |

Primary Examiner—Albert T. Meyers
Assistant Examiner—D. W. Robinson
Attorney, Agent, or Firm—Ladas, Parry, Von Gehr, Goldsmith & Deschamps

[57] ABSTRACT

The compound (bis-diethylamine)2,5-dihydroxybenzene-1,4-disulfonate is useful as a medicament against glaucoma.

3 Claims, 1 Drawing Figure

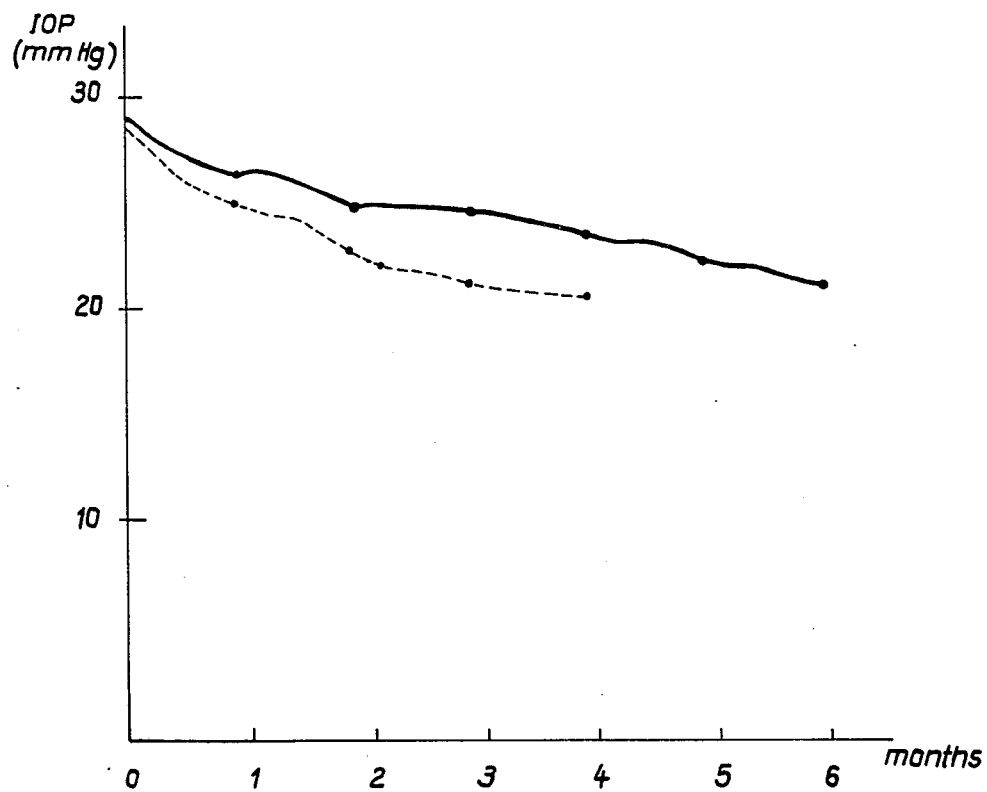

(BIS-DIETHYLAMINE)2,5-DIHYDROXYBENZENE-1,4-DISULFONATE, USEFUL AS A MEDICAMENT AGAINST GLAUCOMA

The compound (bis-diethylamine)2,5-dihydroxybenzene-1,4-disulfonate of formula

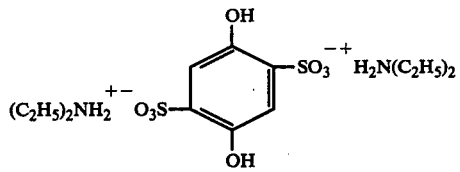

which has the generic international non-proprietary name bis-diethylamine salt of Persylate is known to reduce the bleeding time of the rabbit ear in the test method according to Roskam (see U.S. Pat. No. 4,038,390).

It has now surprisingly be found that this persylate has the ability to lower intra-ocular pressure (IOP).

In an animal model, this persylate was found to have a favorable influence of IOP.

In a study, intra-cameral perfusion with this persylate (400 µg/ml) in 6 anaesthetized rabbits, employing a technique of constant pressure infusion has resulted in a significant increase (57%) in outflow facility.

A clinical trial demonstrated the interest of this persylate in the treatment of glaucoma.

20 patients with chronic simple glaucoma (open-angle glaucoma) were treated during 6 months with a daily dosage of 750 mg of this persylate in tablet form. The individual patient results for IOP before and after treatment are shown in Table I.

The annexed drawing shows the evolution of IOP (mean value of 20 patients results) after the 6 months treatment period with 750 mg of this persylate per day in tablet form.

Also show in this chart is the evolution of the mean value of 10 patients results during 4 months with 1500 mg per day incapsule form. It can be seen that the higher dose allows a faster lowering of IOP.

Useful dosage range: 100 mg – 5 g daily, a higher dose being preferred for initial treatment and a lower dosage for maintenance treatment.

The compound can be administered in any suitable galenic form, such as tablets, injectable solutions, capsules, suppositories, etc.

| | IOP (mm Hg) | |
|---|---|---|
| | Before treatment | After treatment |
| PATIENT NO. | Right/left Eye | Right/left Eye |
| 1 | 28/29 | 22/21 |
| 2 | 26/27 | 20/20 |
| 3 | 30/35 | 23/26 |
| 4 | 36/32 | 29/25 |
| 5 | 30/30 | 23/23 |
| 6 | 23/23 | 16/16 |
| 7 | 27/28 | 20/22 |
| 8 | 30/31 | 23/23 |
| 9 | 29/31 | 23/24 |
| 10 | 28/28 | 19/17 |
| 11 | 31/29 | 23/21 |
| 12 | 28/27 | 22/23 |
| 13 | 33/28 | 22/21 |
| 14 | 30/32 | 19/20 |
| 15 | 28/27 | 22/21 |
| 16 | 30/28 | 22/23 |
| 17 | 29/32 | 22/23 |
| 18 | 27/29 | 21/21 |
| 19 | 32/29 | 23/24 |
| 20 | 31/28 | 24/22 |

What is claimed is:

1. A method of treating a human being suffering from glaucoma, comprising administering in galenic form to said human a pharmaceutically effective amount of (bis-diethylamine)2,5-dihydroxybenzene-1,4-disulfonate in a pharmaceutically acceptable carrier.

2. The method according to claim 1, wherein said pharmaceutically effective amount is from 100 mg to 5 g per day of said (bis-diethylamine) 2,5-dihydroxybenzene-1,4-disulfonate.

3. The method according to claim 2, wherein said (bis-diethylamine) 2,5-dihydroxybenzene-1,4-disulfonate in a pharmaceutically-acceptable carrier is orally administered.

* * * * *